United States Patent
Cooper

[11] Patent Number: 5,175,323
[45] Date of Patent: Dec. 29, 1992

[54] PREPARATION OF ESTERIFIED PROPOXYLATED GLYCERIN BY TRANSESTERIFICATION

[75] Inventor: Charles F. Cooper, Paoli, Pa.

[73] Assignee: Arco Chemical Technology, L.P., Wilmington, Del.

[21] Appl. No.: 227,048

[22] Filed: Aug. 1, 1988

[51] Int. Cl.$^5$ .............................................. C07C 51/00
[52] U.S. Cl. .................................. 554/164; 554/168; 554/169
[58] Field of Search ...................... 260/410.7; 554/168, 554/169, 164

[56] References Cited

U.S. PATENT DOCUMENTS

| | | | |
|---|---|---|---|
| 2,527,970 | 10/1950 | Sokol | 568/620 |
| 2,610,125 | 9/1952 | Volko et al. | 99/123 |
| 3,057,891 | 10/1962 | De Groote | 568/620 |
| 3,337,595 | 8/1967 | Lamont | 260/410.7 |
| 4,517,360 | 5/1985 | Volpenheim | 536/119 |
| 4,518,772 | 5/1985 | Volpenheim | 536/119 |

FOREIGN PATENT DOCUMENTS

| | | | |
|---|---|---|---|
| 0254547 | 1/1988 | European Pat. Off. | |
| 207070 | 2/1984 | Fed. Rep. of Germany | |
| 45-20286 | 7/1970 | Japan | 560/240 |
| 62-185049 | 8/1987 | Japan | 260/410.6 |
| 421063 | 12/1934 | United Kingdom | 260/410.7 |

*Primary Examiner*—José G. Dees
*Assistant Examiner*—Joseph M. Conrad
*Attorney, Agent, or Firm*—Stephen D. Harper

[57] ABSTRACT

A novel method is provided for the preparation of food grade esterified propoxylated glycerin by transesterification in a solventless system by reacting at temperatures of from about 100° C. to about 250° C. a propoxylated glycerin having from 2 to 100 oxypropylene units per glycerin with a saturated or unsaturated C10 to C24 fatty acid ester or mixtures thereof.

24 Claims, No Drawings

PREPARATION OF ESTERIFIED PROPOXYLATED GLYCERIN BY TRANSESTERIFICATION

FIELD OF THE INVENTION

This invention relates to a novel method for the preparation of esterified propoxylated glycerin from lower fatty (C10-C24) esters which are particularly useful as non-caloric food substitutes for edible fats and oils and thus have an acceptable food grace quality.

BACKGROUND OF THE INVENTION

Edible, wholly or partially non-digestible low calorie fat materials and methods for the preparation thereof are known. Much has been written about the adverse health problems of high fat diets, thus indicating clearly an interest in and a need for a fat substitute that is either entirely non-digestible, or has a reduced caloric value. The recent interest in non-caloric food substitutes has resulted in several classes of compounds being proposed. One suggested class has been esterified propoxylated glycerins. However, because the recommended methods of preparation either required toxic catalysts which cannot be completely removed or result in a product with unacceptable acidity, new process methods are needed. The instant invention overcomes these problems.

European Patent No. 254,547 discloses that esterified propoxylated glycerins can be used as non-caloric food substitutes. References cited therein provide a good review of the field relating to fat substitutes, methods for their preparation and problems associated therewith. Two methods of preparation are described in EP 254,547 none of which can be used to prepare a food grade product. The preferred method is to react fatty acids with a propoxylated glycerin using p-toluenesulfonic acid as catalyst allowing catalyst residues at unacceptable levels even after purification. An alternative method, which is exemplified in the examples, reacts the propoxylated glycerin with a fatty acid chloride in the presence of a tertiary amine such as pyridine. Not only would such methods be technically impractical for commercialization but would require column chromatography for any purification.

U.S. Pat. No. 3,337,595 describes a method for preparing fatty esters of propoxylated glycerins where the propoxylated glycerin has a molecular weight above 600. These esters are disclosed as being useful for controlling, suppressing and/or preventing foaming of aqueous systems having foaming tendencies in industrial processes. The process is not suitable for preparing food grade products. The acid values (maximum of 25 KOH/g) are much too high for an edible oil. Only stoichiometric quantities of reactants are employed resulting in a method too slow for a practical commercial process.

U.S. Pat. Nos. 4,517,360 and 4,518,772 describe processes for preparing sucrose polyesters by the catalytic transesterification of sucrose with fatty acid methyl esters in a solventless system wherein part of the fatty acid esters is converted to a fatty acid soap by hydrolysis with an alkali metal hydroxide such as KOH. This in turn required complicated purification where water was added to the reaction product and the mixture centrifuged to remove the soaps and catalyst. The final organic product was purified by vacuum steam stripping and decolorization.

SUMMARY OF THE INVENTION

According to the present process there is provided an improved method for the preparation of food grade esterified propoxylated glycerin by transesterification from (C10-C24) fatty esters such as methyl oleate, in a solventless system without the formation or addition of fatty acid soaps. The removal of any catalyst, if necessary, is by simple filtration procedures.

It is an object of this invention to provide a novel method for the preparation of esterified propoxylated glycerin having food grade quality by transesterification with esters of C10 to C24 saturated or unsaturated fatty acids.

Particular advantages of the method of the instant invention as compared to prior art methods are, a) no free acids are employed and therefore acidity is minimized, b) the use of solvents can be eliminated without any addition of fatty soaps, c) the transesterification can be carried out directly with a propoxylated glycerin prior to potassium or sodium removal without additional catalyst, and d) most of the catalyst can be removed simply by filtration, with the addition of water or centrifugation not required.

These and other objects and advantages of this invention will become apparent from the description of the invention and from the claims.

DETAILED DESCRIPTION OF THE INVENTION

In accordance with the present invention esterified propoxylated glycerins are prepared in a solventless system by reacting at temperatures of from about 100° C. to about 250° C. preferably from 150° C. to 225° C. a propoxylated glycerin having from 2 to 100, preferably from 5 to 25, oxypropylene units per glycerin with a molecular weight range of from about 200 to about 5900, with a saturated or unsaturated C10-C24 fatty acid ester or mixtures thereof, such as soya acid fatty ester, and thereafter subjecting the esterified propoxylated glycerin product to purification to remove any excess fatty ester by, for example, vacuum steam stripping, and any catalyst which may be present by filtration. Decolorization of the product if required can be achieved by heating with activated charcoal or bleaching earths. Should a level of alkali metal, e.g. potassium, below that achieved by filtration be desired, it can be removed by adsorption precipitation with $CO_2$ ion exchange or extraction. Thus, the novel process of this invention involves (1) the propoxylation of glycerin or the use of a propoxylated glycerin per se, (2) transesterification of the propoxylated glycerin, the rate of which can be enhanced by carrying out the reaction under reduced pressures of from about 0.01 mm up to atmospheric, preferably 1 mm to 50 mm of mercury, with gas or low boiling liquid stripping or a combination of the two, (3) simple purification methods to produce a food grade quality esterified propoxylated glycerin.

Propoxylation of glycerin can be carried out by the addition of propylene oxide to glycerin in the presence of a catalytic amount of an alkali metal alkoxylate at temperatures of from about 70° C. to about 130° C. preferably 90° C. to 110° C. and the propylene oxide added at a rate to maintain a pressure in the reactor of about 50 to 60 psi. The alkali metal alkoxylate can generally be prepared by heating at temperatures of from about 100° C. to 110° C. KOH or NaOH with glycerin while continuously removing water, preferably under reduced pressure and is employed in the propoxylation reaction in an amount of from about 0.0003 mol to about 3.3 mol preferably from 0.003 to 1.0 mol of alkali metal content per 100 g. glycerin employed. The degree of propoxylation is controlled and thus the molecular weight, by regulating the amount of propylene oxide fed into the reactor. After the desired molecular weight is reached, the potassium or sodium is normally removed by any suitable method such as adsorption, ion exchange, or extraction. However, should the potassium be removed as described hereinabove, transesterification of the propoxylated glycerin would require that a suitable catalyst such as sodium or potassium alkoxide be added to the reaction system in amounts of from about 0.0005 to about 5.5 meq/g. preferably 0.005 to 1.65 meq/g. of propoxylated glycerin. A particular advantage of the instant invention which is exemplified is that if the potassium or sodium is not removed after preparation of the propoxylated glycerin, additional transesterification catalyst is not required.

The C10-C24 fatty acid esters which may be employed as reactants in the present invention are the C1 to C4 alkyl esters such a methyl or ethyl oleate, etc. and may be saturated or unsaturated fatty acid esters or mixtures thereof. Generally an excess of the fatty acid esters is employed in the reaction system in order to increase the rate of reaction and insure complete conversion of the propoxylated glycerin. Illustrative of such C10-C24 fatty acid esters which may be employed include for example, the saturated C1 to C4 alkyl esters of capric, lauric myristic, pentadecanoic, n-hexadecanoic (palmitic), heptadecanoic, stearic, nonadecanoic, n-eicosanoic, n-docosanoic and n-tetracosanoic acids, as well as the unsaturated C1 to C4 alkyl esters of dodecylenic, palmitoleic, oleic, linoleic, linolenic, eicosenoic, arachidonic, docosahexaenoic and selacholeic acids. As indicated hereinabove, mixtures of the esters either saturated or unsaturated or mixtures of both, may be employed. Fatty acid esters of soya oil containing predominately esters of palmitic (9.8%) stearic (2.4%) oleic (28.9%), linoleic (50.7%) linolenic (6.5%) acids may be employed.

As indicated hereinabove, the tranesterification can be carried out directly on the propoxylated glycerin after formation thereof and prior to the removal of the alkali metal catalyst employed. If the propoxylated glycerin is treated to remove the alkali metal catalyst suitable transesterification catalysts such as the alkali metal alkoxides, e.g. potassium methoxide, having from C1-C4 and preferably C1 or C2 carbon atoms in the alkyl group must be added to the reaction mixture. Potassium or sodium methoxide (potassium or sodium methylate) is the preferred catalyst The reactions of the present invention, i.e., propoxylation, transesterification and purification may be carried out in any suitable reactor which is generally equipped with a means for agitation and a means for regulating temperature and pressure. The reaction may be carried out as a batch or continuous process.

The present invention is more fully illustrated by the following examples, which include particular features of the invention. However, the examples are not to be construed as limiting the invention in any way, it being understood that numerous variations are possible without departing from the spirit and scope of the invention. All parts are in parts by weight unless otherwise indicated.

EXAMPLE 1

Propoxylation of Glycerin 992 parts of glycerin were heated with 80 parts of 85% potassium hydroxide (KOH) solution at 110° C. and 10 mm pressure in a stainless steel stirred autoclave with a dry ice trap for water removal until no further water was being evolved. The reactor was pressurized with nitrogen and cooled to 92° C. and 5170 parts of propylene oxide added on a pressure demand basis maintaining a reactor pressure of 55 psi. After the propylene oxide had been added the reaction was continued for an additional 5 hours. The reactor was then cooled and purged with nitrogen to provide a propoxylated glycerin for transesterification. Potassium was removed from the propoxylated glycerin by heating to 290° C. for 2 hrs. with 10 wt. percent magnesium silicate to give a potassium level of about 5 ppm.

EXAMPLE 2

556 parts (1 mol) of propoxylated glycerin of Example 1 having a hydroxyl number of 290-310 (corrected for basicity) and containing 4.3 parts potassium (0.20% catalyst concentration as potassium methoxide) was heated at 150° C. with 1362 parts methyl oleate for 3 hrs. at 10 mm pressure in a three neck reaction flask equipped with a thermometer and a distilling head (Dean-Stark) for methanol. Hydroxyl conversion was 96%. Titration using bromophenol blue or phenolphthalein shows that after filtration all basicity was removed and the final potassium level of the product was <100 ppm. Excess fatty ester starting material was removed by steam stripping at 200° C. and the product decolorized with 1 wt. percent charcoal.

EXAMPLES 3-10

The procedure of Example 2 was repeated with methyl oleate and employing a propoxylated glycerin from which the potassium was essentially removed with magnesium silicate to provide a final potassium level of about 5 ppm and thus requiring the addition of a transesterification catalyst. The results and conditions are set forth in Table 1 below showing % conversion (OH).

TABLE 1

| Ex. No. | MO:Prop.G* (Molar ratio) | Cat. | Cat. Conc. (Meq/g Prop.G) | Temp. (°C.) | Time Hrs. | Press mm | % Conv. (OH) |
|---|---|---|---|---|---|---|---|
| 3 | 1:1.10 | NaOMe | 0.43 | 175 | 5.0 | 15 | 95 |
| 4 | 1:1.00 | KOMe | 0.39 | 150 | .075 | 18 | 80 |
| 5 | 1:1.06 | KOMe | 0.21 | 125 | 5.1 | 32 | 86 |
| 6 | 1:1.06 | NaOMe | 0.21 | 125 | 5.0 | 29 | 84 |
| 7 | 1:1.15 | KOMe | 0.21 | 125 | 5.0 | 28 | 81 |
| 8 | 1:1.15 | KOMe | 0.21 | 170 | 5.3 | 28 | 90 |
| 9 | 1:1.15 | KOMe | 0.21 | 200 | 5.7 | 18 | 96 |

TABLE 1-continued

| Ex. No. | MO:Prop.G* (Molar ratio) | Cat. | Cat. Conc. (Meq/g Prop.G) | Temp. (°C.) | Time Hrs. | Press mm | % Conv. (OH) |
|---|---|---|---|---|---|---|---|
| 10 | 1:1.15 | KOMe | 0.20 | 200 | 6.3 | 10 | 99 |

*MO = Methyl Oleate
Prop.G. = Propoxylated Glycerin
NaOMe = Sodium Methoxide
KOMe = Potassium Methoxide

EXAMPLES 11-18

The general procedure of Example 2 for transesterification was carried out without the addition of any transesterification methoxide catalyst. After the preparation of the propoxylated glycerin according to the procedure set forth in Example 1, the product was not subjected to purification to remove the potassium and was directly employed containing the propoxylation alkoxylate catalyst in transesterification with methyl oleate. The results and conditions are set forth in Table 2 below.

TABLE 2

| Ex. No | MO:Prop.G (Molar ratio) | Cat. Conc. (Meq/g.Prop.G) | Temp. (°C.) | Time Hrs. | Press mm | % Conv. (OH) |
|---|---|---|---|---|---|---|
| 11 | 1:1.22 | 0.21 | 200 | 5.6 | 18 | 97 |
| 12 | 1:1.22 | 0.45 | 150 | 6.5 | 10 | 94 |
| 13 | 1:1.22 | 0.45 | 125 | 24.0 | 12 | 95 |
| 14 | 1:1.15 | 0.21 | 200 | 6.4 | 9 | 99 |
| 15 | 1:1.15 | 0.11 | 200 | 6.6 | 8 | 87 |
| 16 | 1:1.06 | 0.21 | 200 | 16.9 | 15 | 90 |
| 17 | 1:1.06 | 0.21 | 150 | 35.0 | 7 | 93 |
| 18 | 1:1.15 | 0.00 | 200 | 5.5 | 9 | 7 |

EXAMPLES 19-24

The procedure of Example 2 was repeated with methyl oleate and a propoxylated glycerin from which the propoxylation alkoxylate catalyst was removed by filtration but using various catalyst systems and to show, in some cases, the effect of water on the reaction. The results based on % conversion of OH groups and conditions are set forth in Table 3 below. Example 22 employed the propoxylated glycerin directly without alkoxylate catalyst removal but with added water.

TABLE 3

| Ex. No. | MO:Prop.G (Molar ratio) | Catalyst | Water (Wt. %) | Cat. Conc. (Meq/g.Prop.G) | Temp. (°C.) | Time Hrs. | Press mm | % Conv (OH) |
|---|---|---|---|---|---|---|---|---|
| 19 | 1:1.15 | KOH | 0 | 0.21 | 200 | 6 | 22-192 | 50 |
| 20 | 1:1.15 | KOMe/0.5 H$_2$O | 0.5 | 0.22 | 200 | 7 | 12-250 | 73 |
| 21 | 1:1.15 | KOMe/0.5 H$_2$O | 0.5 | 0.22 | 200 | 14 | 10-12 | 77 |
| 22 | 1:1.15 | Prop. G Alkoxylate | 0.4 | 0.21 | 200 | 7.2 | 10-12 | 80 |
| 23 | 1:1.15 | KC$_2$H$_3$O$_2$ | 0 | 0.15 | 200 | 5 | 10 | 66 |
| 24 | 1:1.15 | KC$_2$H$_3$O$_2$ | 0 | 0.30 | 200 | 4.2 | 10-17 | 69 |

EXAMPLE 25-30

Esterified propoxylated glycerin products which contained approximately 1000 to 4000 ppm potassium were filtered without any solvent through diatomaceous earth ("Celite" of Johns-Manville Products Corp.). X-ray analysis was used to analyze any residual potassium content. The filtered product of Examples 28 and 30 were additionally heated with 0.01 parts magnesium silicate and 0.01 parts water per part product for 2 hrs at 90° C., filtered and analyzed for potassium. The results of the catalyst removal are set forth in Table 4.

TABLE 4

| | Potassium Level of Product | |
|---|---|---|
| Ex. No. | Initial | Final |
| 25 | 3700 | 51 |
| 26 | 2100 | 58 |
| 27 | 936 | 110 |
| 28 | 970 | 5 |
| 29 | 927 | 44 |
| 30 | 927 | 3 |

EXAMPLE 31

50 g of 4685 mol weight propoxylated glycerin containing approximately 79 oxypropylene oxide units per glycerin and having a hydroxyl number of 36 from which the propoxylation catalyst had been essentially removed, were mixed with 40 g of methyl oleate and 0.7 g of potassium methoxide. The mixture was heated to 20° C. at 10 mm pressure for 7 hours in a three neck reaction flask equipped with a thermometer and a "Dean-Stark" trap for removing methanol continuously. The final product weighing 85g (representing a 96% yield) was filtered and heated with 0.5 g of magnesium silicate ("Magnesol" of the FMC Corporation) for 2 hours at 90° C. The magnesium silicate was removed by filtration and excess methyl oleate by vacuum steam stripping. The product was analyzed for hydroxyl number and was found to be 93% triester (2.2 mg KOH/g hydroxyl number).

EXAMPLE 32

The procedure of Example 31 was repeated by heating at 150° C. 50 g of 3000 mol weight propoxylated glycerin from which the propoxylation catalyst had been essentially removed (containing 52 oxypropylene units per glycerin and having 54 mg KOH/g hydroxyl number) with 30 g methyl oleate and 0.70 g potassium methoxide. After 3 hours reaction time at 150° C., the transesterified product was purified as in Example 31. The hydroxyl number was 1.4 mg KOH/g (97% conversion).

EXAMPLE 33

The procedure of Example 31 was repeated by heating at 50° C. for 3 hours, 50 g of 2000 mol weight propoxylated glycerin from which the propoxylation catalyst had been removed (hydroxyl number of 87 mg KOH/g) with 35 g methyl oleate and 0.70g potassium methoxide. The product was purified as in Example 31 and analyzed to show a final hydroxyl number of 0.9 mg KOH/g (98% conversion).

EXAMPLE 34

The procedure of Example 31 was repeated by heating at 150° C. for 3 hours, 50 g of 556 mol weight propoxylated glycerin from which the propoxylation catalyst had been removed and having a 300 mg KOH/g hydroxyl number with 120 g soya acid fatty methyl ester (obtained commercially from Emery Chemicals) and 0.70 g potassium methoxide. Upon completion of the reaction, excess fatty ester was removed by vacuum steam distillation at less than 10 torr pressure at 200° C. The hydroxyl number was 3.5 mg KOH/g representing greater than a 97% conversion.

EXAMPLE 35

The procedure of Example 31 was repeated by heating at 150° C. for 3 hours, 556 g (556 mol weight) essentially catalyst free propoxylated glycerin (300 mg KOH/g hydroxyl number) with 1720g methyl tetracosanoate and 0.70 g potassium methoxide at 10 torr pressure. After the reaction, the excess methyl fatty ester was removed by vacuum steam distillation at less than 10 torr pressure at 200° C. Analysis showed a hydroxyl number of less than 3.0 mg KOH/g representing greater than 97% conversion

EXAMPLE 36

The procedure of Example 31 was repeated by heating at 150° C. for 3 hours, 50 g of 556 mol weight essentially catalyst free propoxylated glycerin (300 mg KOH/g hydroxyl number) with 120g methyl stearate and 0.70 g potassium methoxide at 10 torr pressure. Upon completion of reaction the excess methyl stearate was removed by vacuum distillation at 10 torr pressure at 200° C. The hydroxyl number by analysis was less than 2.0 mg KOH/g representing greater than 98% conversion.

I claim:

1. A method for preparation of an esterified propoxylated glycerin in a solventless reaction system which comprises the steps of:

propoxylating glycerin at a temperature of from about 70° to about 130° with propylene oxide in the presence of an alkali metal alkoxylate catalyst in an amount of from about 0.0003 mol to about 3.3 mol of alkali metal content per 100 g glycerin employed to give a propoxylated glycerin having from 2 to 100 oxypropylene units per glycerin;

transesterifying the propoxylated glycerin directly, without any removal of the alkali metal alkoxylate catalyst, at a temperature of from about 100° C. to about 250° C. with a saturated or unsaturated C10 to C24 fatty acid C1 to C4 alkyl ester or mixtures thereof to provide an esterified propoxylated glycerin product; and purifying the propoxylated glycerin product by vacuum steam stripping said product to remove any unreacted fatty acid ester and filtering to essentially remove and reduce the alkali metal content to provide a food grade esterified propoxylated glycerin.

2. A method according to claim 1 wherein the alkali metal alkoxylate catalyst is employed in an amount of from 0.003 to 1.0 mol of alkali metal content per 100 g glycerin employed.

3. A method according to claim 1 wherein the transesterification is carried out under a reduced pressure of from about 0.01 mm up to about atmospheric.

4. A method according to claim 1 wherein the transesterification is carried out under a reduced pressure of from 1 mm to 50 mm of mercury.

5. A method according to claim 1 wherein the propoxylation is carried out at a temperature of from 90° C. to 110° C.

6. A method according to claim 1 wherein the propoxylated glycerin has from 5 to 25 oxypropylene oxide units per glycerin.

7. A method according to claim 1 wherein the transesterification is carried out at a temperature of from 150° C. to 225° C.

8. A method according to claim 1 wherein the alkali metal alkoxylate catalyst is potassium alkoxylate.

9. A method according to claim 1 wherein the fatty acid alkyl ester is selected from the group consisting of methyl oleate, soya acid fatty methyl ester, methyl stearate, and methyl tetracosanoate.

10. A method according to claim 9 wherein the fatty acid alkyl ester is methyl oleate.

11. A method according to claim 1 wherein the esterified propoxylated glycerin product is decolorized.

12. A method for preparation of an esterified propoxylated glycerin in a solventless reaction system which comprises the steps of:

propoxylating glycerin at a temperature of from about 70° to about 130° with propylene oxide in the presence of an alkali metal alkoxylate catalyst in an amount of from about 0.0003 mol to about 3.3 mol of alkali metal content per 100 g glycerin employed to give a propoxylated glycerin having from 2 to 100 oxypropylene units per glycerin;

removing the alkali metal alkoxylate catalyst from the propoxylated glycerin;

transesterifying the propoxylated glycerin at a temperature of from about 100° C. to about 250° C. with a saturated or unsaturated C10 to C24 fatty acid C1 to C4 alkyl ester or mixtures thereof in the presence of an alkali metal alkoxide catalyst having from 1 to 4 carbon atoms in the alkyl group in an amount of from about 0.0005 to about 5.5 meq/g of propoxylated glycerin to provide an esterified propoxylated glycerin product; and purifying the propoxylated glycerin product by vacuum steam stripping said product to remove any unreacted fatty acid ester and filtering to essentially remove and reduce the alkali metal alkoxide to provide a food grade esterified propoxylated glycerin.

13. A method according to claim 12 wherein the alkali metal alkoxylate catalyst is employed in an amount of from 0.0003 to 1.0 mol of alkali metal content per 100 g glycerin employed.

14. A method according to claim 12 wherein the alkali metal alkoxide catalyst is employed in an amount of from 0.0005 to 1.65 meq/g of propoxylated glycerin.

15. A method according to claim 12 wherein the transesterification is carried out under a reduced pressure of from about 0.01 mm up to about atmospheric.

16. A method according to claim 12 wherein the transesterification is carried out under a reduced pressure of from 1 mm to 50 mm of mercury.

17. A method according to claim 12 wherein the propoxylation is carried out at a temperature of from 90° C. to 110° C.

18. A method according to claim 12 wherein the propoxylated glycerin has from 5 to 25 oxypropylene units per glycerin.

19. A method according to claim 12 wherein the transesterification is carried out at a temperature of from 150° C. to 225° C.

20. A method according to claim 12 wherein the alkali metal alkoxylate catalyst is potassium alkoxylate.

21. A method according to claim 12 wherein the alkali metal alkoxide catalyst is potassium or sodium methoxide.

22. A method according to claim 12 wherein the fatty acid alkyl ester is selected from the group consisting of methyl oleate, soya acid fatty methyl ester, methyl stearate, and methyl tetracosanoate.

23. A method according to claim 22 wherein the fatty acid alkyl ester is methyl oleate.

24. A method according to claim 12 wherein the esterified propoxylated glycerin product is decolorized.

* * * * *